US00PP09016P

United States Patent [19]

Olesen et al.

[11] Patent Number: Plant 9,016

[45] Date of Patent: Dec. 20, 1994

[54] MINIATURE ROSE PLANT NAMED POULSTAR

[75] Inventors: Mogens N. Olesen; Pernille Olesen, both of Fredensborg, Denmark

[73] Assignee: Bear Creek Gardens, Inc., Medford, Oreg.

[21] Appl. No.: 209,869

[22] Filed: Mar. 11, 1994

[51] Int. Cl.[5] ..... A01H 5/00

[52] U.S. Cl. ..... Plt./8.1

[58] Field of Search ..... Plt. 8.1, 1

*Primary Examiner*—Howard J. Locker

*Attorney, Agent, or Firm*—Klarquist, Sparkman, Campbell, Leigh & Whinston

[57] ABSTRACT

A miniature rose plant having attractive, pure white flower color; dark green, disease-resistant foliage; ease of propagation by softwood cuttings; compact dwarf growth habit; and suitability for pot culture.

1 Drawing Sheet

The present invention relates to a new and distinct variety of rose plant of the miniature class which was originated by us by crossing the variety POULvita (unpatented) with an unnamed seedling.

The primary objective of this breeding was to produce a healthy, hardy, new rose variety having a dwarf habit; pure white flower color; ability to grow well from cuttings; and adaptability to pot culture. The objective was substantially achieved, along with other desirable improvements, as evidenced by the following unique combination of characteristics that are outstanding in the new variety and that distinguish it from its parents, as well as from all other varieties of which we are aware:

1. Clean, white flowers;
2. Compact dwarf habit;
3. Healthy, dark green, disease-resistant foliage;
4. Ease of propagation from softwood cuttings; and
5. Adaptability to pot culture.

Asexual reproduction of this new variety by softwood cuttings as performed at Wasco and Somis, Calif., and Fredensborg, Denmark, shows that the foregoing characteristics and distinctions come true to form and are established and transmitted through succeeding propagations.

The accompanying illustration shows typical specimens of the vegetative growth and flowers of this new variety in different stages of development, depicted in color as nearly true as it is reasonably possible to make the same in a color illustration of this character.

The following is a detailed description of our new rose cultivar with color descriptions using terminology in accordance with The Royal Horticultural Society (London) Colour Chart, except where ordinary dictionary significance of color is indicated.

Parentage:

*Seed parent.*—POULvita.

*Pollen parent.*—Unnamed seedling.

Classification:

*Botanical.*—*Rosa hybrida.*

*Commercial.*—Miniature.

FLOWER

Observations made from specimens grown in greenhouse environments at Somis, Calif., and Fredensborg, Denmark.

Blooming habit: Recuurent.

Bud:

*Size.*—13 mm long when the petals start to unfurl.

*Form.*—The bud form is short, pointed ovoid.

*Color.*—When sepals first divide, bud color is White Group 155D. When half blown, the upper and lower sides of the petals are White Group 155D.

*Sepals.*—Color: Green Group 138B. Surface texture: Covered in fine hairs. There are three normally appendaged sepals. There are two unappendaged sepals with hairy edges.

*Receptacle.*—Color: Green Group 137D. Shape: Funnel. Size: Small (3 mm×4 mm). Surface: Smooth.

*Peduncle.*—Length: Short (3.7 cm). Surface: Smooth. Color: Medium green. Strength: Stiff, erect.

Bloom:

*Size.*—Small. Average open size is 2.5 cm.

*Borne.*—Singly and several together, in rounded clusters of 3 to 5 flowers.

*Stems.*—Short (13 to 15 cm); strong.

*Form.*—When first open: High centered. Permanence: Flattens, all petals curl, quill fashion.

*Petalage.*—Number of petals under normal conditions: 25.

*Color.*—The upper and reverse sides of the petals are White Group 155D. The base of each petal is White Group 155D. The major color on the upper side is White Group 155D.

*Variegations.*—None.

*Discoloration.*—The general tonality at the end of the first and third days: No change.

*Fragrance.*—Slight.

Petals:

*Texture.*—Thin.

*Shape.*—Oval.

*Form.*—Tips slightly recurved, edges slightly quilled.

*Arrangement.*—Imbricated, with few petaloids in the center.

*Persistence.*—Drop off cleanly.

*Lastingness.*—On the plant: Long (9 to 12 days). As a cut flower: Long (7 days).

Reproductive parts:

Anthers.—Size: Small. Quantity: Many. Color: Yellow. Arrangement: Regular around styles.

*Filaments.*—Color: White.

*Pollen.*—Color: Gold yellow.

*Styles.*—Color: Greenish white.

*Stigmas.*—Color: Greenish white.

Form: Bush.

Growth: Vigorous, dwarf, upright, branching. Height outdoors is 41 to 46 cm×30 cm wide.

Foliage:

*Number of leaflets on normal mid-stem leaves.*—5.

*Size.*—Small (6 cm×4 cm).

*Quantity.*—Normal.

*Color.*—New foliage: Reddish green. Old foliage: Green Group 137A.

Leaflets:

*Shape.*—Pointed oval.

*Texture.*—Upper side: glossy, smooth.

*Edge.*—Serrated.

*Serration.*—Single, small.

*Petiole rachis.*—Color: Green.

*Petiole underside.*—Smooth, with occasional prickles.

*Stipules: Short, bearded.*

*Disease resistance.*—Resistant to mildrew and rust under normal growing conditions at Somis, Calif.

Wood:

*New wood.*—Color: Light green. Bark: Smooth.

*Old wood.*—Color: Green. Bark: Smooth.

Prickles:

*Quantity.*—On main canes from base: Few. On laterals from main canes: Few.

*Form.*—Short (3 mm); straight.

*Color when young.*—Green.

Small prickles:

*Quantity.*—On main stalks: None. On laterals: None.

We claim:

1. A new and distinct variety of rose plant of the miniature class, substantially as herein shown and described, characterized particularly as to novelty by the unique combination of its attractive, pure white flower color; dark green, disease-resistant foliage; ease of propagation by softwood cuttings; compact dwarf growth habit; and suitability for pot culture.

* * * * *

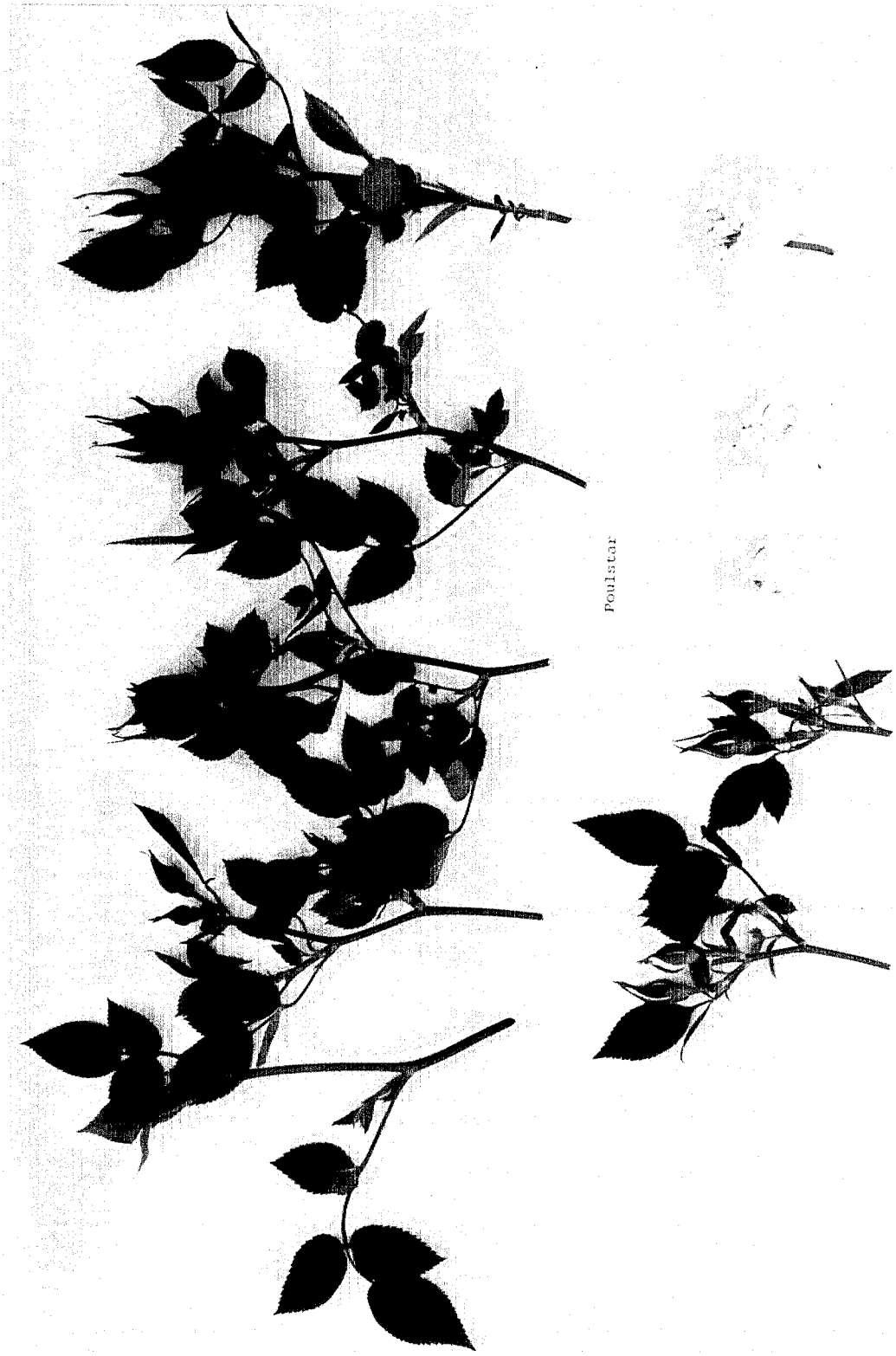
Poulstar